United States Patent
Bacher et al.

(10) Patent No.: US 9,782,063 B2
(45) Date of Patent: Oct. 10, 2017

(54) OPTICAL COUPLING EFFICIENCY DETECTION ASSEMBLY AND METHOD OF ASSEMBLING THE SAME

(71) Applicant: Novartis AG, Basel (CH)

(72) Inventors: Gerald David Bacher, Carlsbad, CA (US); Ronald T. Smith, Irvine, CA (US)

(73) Assignee: Novartis AG, Basel (CH)

( * ) Notice: Subject to any disclaimer, the term of this patent is extended or adjusted under 35 U.S.C. 154(b) by 209 days.

(21) Appl. No.: 14/571,389

(22) Filed: Dec. 16, 2014

(65) Prior Publication Data

US 2016/0166139 A1  Jun. 16, 2016

(51) Int. Cl.
| | |
|---|---|
| G02B 6/00 | (2006.01) |
| A61B 3/00 | (2006.01) |
| G02B 6/42 | (2006.01) |
| F21V 8/00 | (2006.01) |
| A61B 90/30 | (2016.01) |

(52) U.S. Cl.
CPC .......... *A61B 3/0008* (2013.01); *G02B 6/0006* (2013.01); *G02B 6/4214* (2013.01); *G02B 6/4225* (2013.01); *A61B 2090/306* (2016.02); *A61B 2560/0276* (2013.01); *A61B 2562/146* (2013.01); *A61B 2562/228* (2013.01); *G02B 6/4286* (2013.01); *G02B 6/4292* (2013.01)

(58) Field of Classification Search
CPC .......... A61B 1/06; A61B 1/07; G02B 6/0006; G02B 6/4225; G02B 6/4214; G02B 6/4286; G02B 6/4292
USPC ....................................................... 600/249
See application file for complete search history.

(56) References Cited

U.S. PATENT DOCUMENTS

| | | | |
|---|---|---|---|
| 5,039,191 A | 8/1991 | Myszka | |
| 5,396,571 A * | 3/1995 | Saadatmanesh | ..... G02B 6/2848 385/33 |
| 5,463,710 A | 10/1995 | Filgas et al. | |

(Continued)

FOREIGN PATENT DOCUMENTS

| | | |
|---|---|---|
| EP | 1265087 A2 | 12/2002 |
| EP | 1265087 A3 | 2/2005 |

(Continued)

OTHER PUBLICATIONS

International Searching Authority, International Search Report, PCT/US2015/064982, Mar. 21, 2016, 5 pages.

(Continued)

*Primary Examiner* — Nicholas Plionis

(57) ABSTRACT

An optical coupling efficiency detection assembly includes a first housing accommodating a beam splitter and a fiber port, a second housing accommodating a ferrule enclosing a monitoring fiber, and an attachment block attaching the first housing to the second housing to establish a parfocal arrangement among the beam splitter, the fiber port, and the ferrule. Further, an assembly method for the optical coupling efficiency detection assembly is disclosed. The assembly method may include providing a beam splitter and a fiber port in a first housing, providing a ferrule enclosing a monitoring fiber in a second housing, and attaching the second housing to the first housing via an attachment block to establish a parfocal arrangement among the beam splitter, the fiber port, and the ferrule.

16 Claims, 13 Drawing Sheets

(56) References Cited

U.S. PATENT DOCUMENTS

| | | |
|---|---|---|
| 5,815,626 A | 9/1998 | Kuba et al. |
| 5,999,255 A | 12/1999 | Dupee et al. |
| 7,292,323 B2 | 11/2007 | Artsyukhovich et al. |
| 8,371,695 B2 | 2/2013 | Papac et al. |
| 8,474,977 B2 | 7/2013 | Hahn et al. |
| 8,542,962 B2 | 9/2013 | Smith et al. |
| 8,561,280 B2 | 10/2013 | Diao et al. |
| 8,662,670 B2 | 3/2014 | Papac et al. |
| 9,107,730 B2 | 8/2015 | Huculak et al. |
| 2001/0055462 A1 | 12/2001 | Seibel |
| 2002/0028049 A1 | 3/2002 | Bartur et al. |
| 2003/0147601 A1 | 8/2003 | Bartur et al. |
| 2008/0183160 A1 | 7/2008 | Papac et al. |
| 2008/0269728 A1 | 10/2008 | Buczek et al. |
| 2008/0291432 A1 | 11/2008 | Horvath et al. |
| 2011/0292344 A1 | 12/2011 | Papac et al. |
| 2012/0203075 A1 | 8/2012 | Horvath et al. |
| 2014/0334781 A1* | 11/2014 | Fiorentino ............ G02B 6/3855 385/78 |
| 2015/0366432 A1 | 12/2015 | Artsyukhovich et al. |

FOREIGN PATENT DOCUMENTS

| | | |
|---|---|---|
| EP | 1949877 B1 | 6/2012 |
| WO | 99/63370 A2 | 12/1999 |
| WO | 2014/145465 A2 | 9/2014 |
| WO | 2014/182212 A1 | 11/2014 |
| WO | 2016/032797 A1 | 3/2016 |
| WO | 2016100082 A1 | 6/2016 |

OTHER PUBLICATIONS

Nternational Searching Authority, Written Opinion of the International Searching Authority, PCT/US2015/064982, Mar. 21, 2016, 6 pages.

PCT/IB2016/052513; International Search Report, International Searching Authority, Jul. 11, 2016, 4 pgs.

PCT/IB2016/052513; Written Opinion, International Searching Authority, Jul. 11, 2016, 6 pgs.

International Searching Authority, International Search Report, PCT/US2015/045641, Dec. 7, 2015, 5 pages.

International Searching Authority, Written Opinion of the International Searching Authority, PCT/US2015/045641, Dec. 7, 2015, 8 pages.

Smith, Ronald T., Prosecution History, U.S. Appl. No. 14/468,696, filed Aug. 26, 2014, 109 pages.

Papac, Michael J., Prosecution History, U.S. Appl. No. 14/840,349, filed Aug. 31, 2015, 51 pages.

\* cited by examiner

US 9,782,063 B2

OPTICAL COUPLING EFFICIENCY DETECTION ASSEMBLY AND METHOD OF ASSEMBLING THE SAME

BACKGROUND

The devices, systems, and methods disclosed herein relate generally to the detection of coupling efficiency of a light beam directed into an optical fiber.

Ophthalmic endo-illumination probes are used to provide illumination in ophthalmic surgeries. In particular, an ophthalmic endo-illumination probe may be inserted into an eye to provide illumination inside the eye during an ophthalmic surgery. Typically, the ophthalmic endo-illumination probe is connected to an optical port of an ophthalmic endo-illumination system to receive light from the ophthalmic endo-illumination system. The ophthalmic endo-illumination system may include a light source that produces light and a condenser that couples the light into an optical fiber of the ophthalmic endo-illumination probe.

During the assembly of the ophthalmic endo-illumination system, the position and tilt of the light beam from the condenser is adjusted until a coupling efficiency of the light beam into the ophthalmic endo-illumination probe connected at the optical port reaches an optimal value. Then, the assembly of the optical port is fixed or immobilized to maintain the coupling position and the coupling efficiency of the light beam into the ophthalmic endo-illumination probe. Nevertheless, various factors may cause the coupling position to move during the assembly process which results in a loss of coupling efficiency.

The present disclosure is directed to devices, systems, and methods that address one or more of the disadvantages of the prior art.

SUMMARY

In an exemplary aspect, the present disclosure is directed to an optical coupling efficiency detection assembly. The optical coupling efficiency detection assembly may include a first housing configured to accommodate a beam splitter and a fiber port, a second housing configured to accommodate a ferrule enclosing a monitoring fiber, and an attachment block having a plurality of planar sides, the first attachment block being rigidly attached to the first housing on a first side of the plurality of planar sides, the first attachment block being rigidly attached to the second housing on a second side of the plurality of planar sides. The second side is adjacent the first side and the first and second housings are positioned on the attachment block in a manner establishing a parfocal arrangement among the beam splitter, the fiber port, and the ferrule.

The optical coupling efficiency detection assembly also may include a condenser configured to direct a light beam into the beam splitter. The beam splitter is configured to split the light beam into a first beam which is coupled into an optical fiber at the fiber port and a second beam which is coupled into the monitoring fiber at the ferrule.

In an aspect, the attachment block may include a first side configured to interface with the first housing and a second side configured to interface with the second housing. The first side is perpendicular to the second side. The first side of the attachment block may include a first attachment surface and first abutment pads protruding from the first attachment surface, and the second side of the attachment block may include a second attachment surface and second abutment pads protruding from the second attachment surface. The first abutment pads of the first side are configured to contact the first housing when the attachment block is attached to the first housing. The second abutment pads of the second side are configured to contact the second housing when the attachment block is attached to the second housing.

In an aspect, the first attachment surface of the first side is bonded to the first housing by a bonding adhesive and the second attachment surface of the second side is bonded to the second housing by the bonding adhesive. The first abutment pads are disposed along a perimeter portion of the first attachment surface and the bonding adhesive is disposed on a center portion of the first attachment surface without interfering with the first abutment pads. Similarly, the second abutment pads are disposed along a perimeter portion of the second attachment surface and the bonding adhesive is disposed on a center portion of the second attachment surface without interfering with the second abutment pads.

In another exemplary aspect, the present disclosure is directed to an assembly method for an optical coupling efficiency detection assembly. The assembly method may include providing a beam splitter and a fiber port in a first housing, providing a ferrule enclosing a monitoring fiber in a second housing, rigidly attaching the first housing to a planar first side of an attachment block, and rigidly attaching the second housing to a planar second side of the attachment block that is adjacent to the first side of the attachment block to establish a parfocal arrangement among the beam splitter, the fiber port, and the ferrule. The assembly method also may include positioning the second housing relative to the first housing to form the parfocal arrangement, and immobilizing the second housing relative to the first housing by bonding the attachment block to the first housing and the second housing.

In an aspect, the positioning step of the assembly method may include directing a light beam from a condenser into the beam splitter to split and couple the light beam simultaneously into an alignment fiber installed at the fiber port and the monitoring fiber at the ferrule, adjusting a position of the condenser to align the light beam with the beam splitter and the fiber port, detecting a coupling efficiency at the monitoring fiber, and adjusting a position of the second housing to optimize the coupling efficiency at the monitoring fiber.

In an aspect, the immobilizing step of the assembly method may include applying a bonding adhesive on a first attachment surface of the attachment block, applying the bonding adhesive on a second attachment surface of the attachment block, and positioning the first attachment surface to the first housing and the second attachment surface to the second housing to bond the attachment block to the first housing and the second housing.

In an aspect, first abutment pads disposed on the first attachment surface contact the first housing and second abutment pads disposed on second attachment surface contact the second housing when the attachment block is attached to the first housing and the second housing. The first abutment pads are disposed along a perimeter portion of the first attachment surface and the second abutment pads are disposed along a perimeter portion of the second attachment surface. The bonding adhesive is titrated on a center portion of the first attachment surface and a center portion of the second attachment surface, such that the bonding adhesive does not interfere with the first and the second abutment pads.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
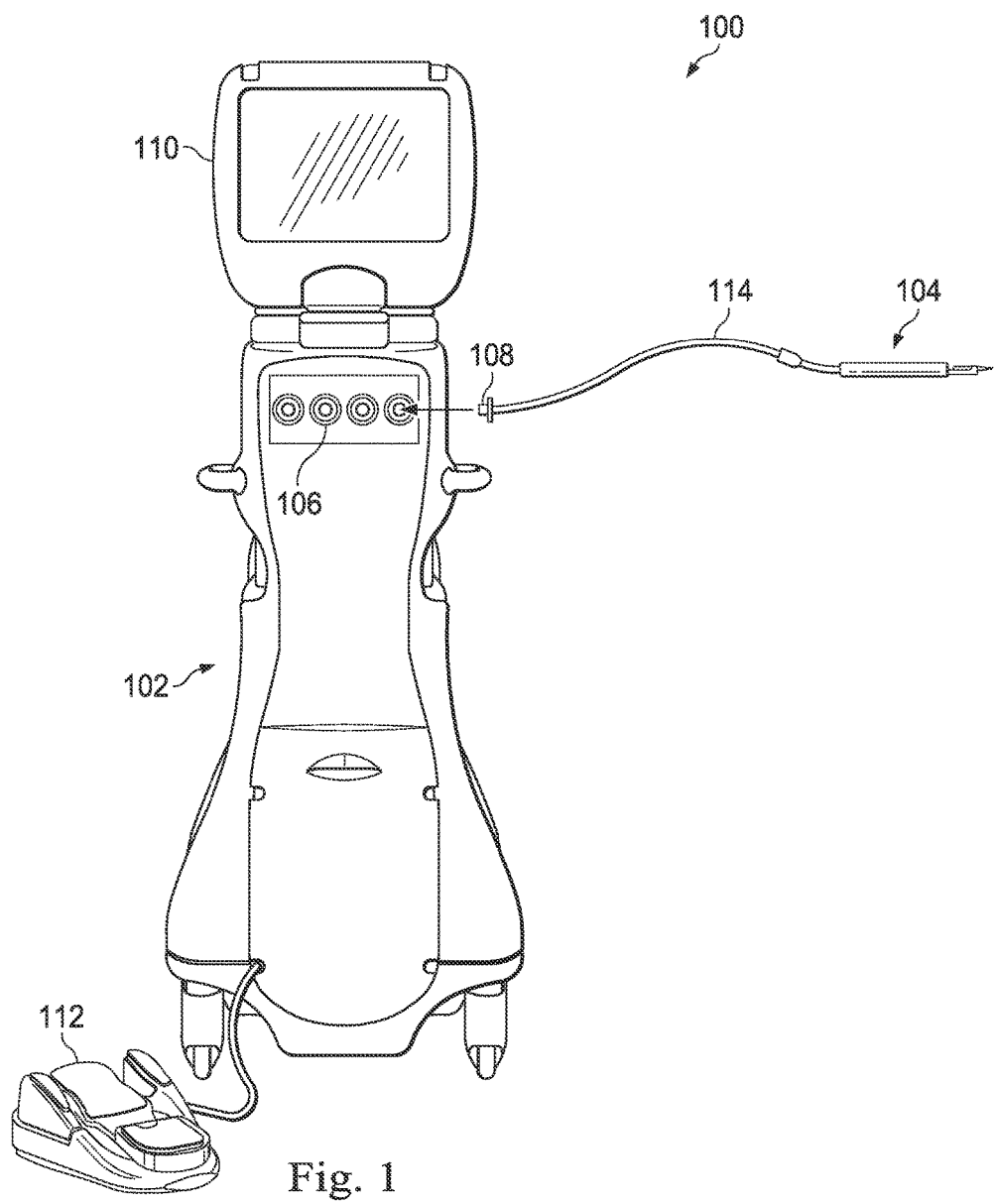
FIG. 1 illustrates a perspective view of an exemplary surgical system according to one embodiment consistent with the principles of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The devices, systems, and methods described herein provide an ophthalmic endo-illumination system including an optical coupling efficiency detection assembly configured to detect an optical coupling efficiency of a light beam coupled into an ophthalmic fiber probe. The optical coupling efficiency detection assembly may include a first housing accommodating a beam splitter and a fiber port, a second housing accommodating a ferrule enclosing a monitoring fiber, and an attachment block attaching the first housing to the second housing to establish a parfocal arrangement among the beam splitter, the fiber port, and the ferrule.

The attachment block is a precisely sized intermediate support that interfaces with both the first and second housings, and maintains a parfocal arrangement between the first and second housings. The first and second housings are each fixed in place on the attachment block to secure their relative positions.

In particular, the attachment block may include a first side configured to interface with the first housing and a second side configured to interface with the second housing. The first side is perpendicular to the second side. The first side of the attachment block may include a first attachment surface and first abutment pads protruding from the first attachment surface and the second side of the attachment block may include a second attachment surface and second abutment pads protruding from the second attachment surface. The first abutment pads of the first side are configured to contact the first housing when the attachment block is attached to the first housing. The second abutment pads of the second side are configured to contact the second housing when the attachment block is attached to the second housing.

The first and second abutment pads are rigid, substantially incompressible pads that act as spacers to separate the side surfaces of the attachment block from the first and second housings. This space can then be filled with a bonding adhesive, which can cure, and because of the rigid and incompressible nature of the abutment pads, the spacing remains unchanged during the curing process.

As described herein, the first attachment surface of the first side is bonded to the first housing by a bonding adhesive and the second attachment surface of the second side is bonded to the second housing by the bonding adhesive. The first abutment pads are disposed along a perimeter portion of the first attachment surface and the bonding adhesive is disposed on a center portion of the first attachment surface without interfering with the first abutment pads. Similarly, the second abutment pads are disposed along a perimeter portion of the second attachment surface and the bonding adhesive is disposed on a center portion of the second attachment surface without interfering with the second abutment pads. Thus, the abutment pads may provide precise contact between the attachment block and the first and second housings to reduce misalignment during the assembly process.

In another aspect, the present disclosure is directed to an assembly method for an optical coupling efficiency detection assembly. The assembly method may include attaching the second housing to the first housing via the attachment block to establish a parfocal arrangement among the beam splitter, the fiber port, and the ferrule. The assembly method also may include positioning the second housing relative to the first housing to form the parfocal arrangement, and immobilizing the second housing relative to the first housing by bonding the attachment block to the first housing and the second housing.

In an aspect, the immobilizing step of the assembly method may include applying the bonding adhesive on the first attachment surface of the attachment block and applying the bonding adhesive on the second attachment surface of the attachment block. In particular, the bonding adhesive is titrated on a center portion of the first attachment surface and a center portion of the second attachment surface, such that the bonding adhesive does not interfere with the first and the second abutment pads. Thus, the abutment pads may provide precise contact without interference from the bonding adhesive to reduce misalignment during the assembly process.

FIG. 1 illustrates an exemplary surgical system, generally designated 100. The surgical system 100 may include a surgical utility supplying device 102 with an associated display screen 110 showing data relating to system operation and performance during a surgical procedure. The surgical system 100 also may include a surgical implement 104 configured to be connected to the surgical utility supplying device 102 via a surgical utility connector 108. The surgical utility supplying device 102 may supply various utility, such as imaging light, illumination light, compressed air, vacuum, pressurized liquid, or the like, to various kinds of surgical implements. For example, the surgical utility supplying device 102 may supply visible light to an ophthalmic fiber probe or may supply compressed air to a surgical vitrectomy probe. A user, e.g., a surgeon, may perform surgeries by using the surgical implements. The surgical utility supplying device 102 may include one or more utility ports 106 each configured to output a certain type of utility. For example, the surgical utility supplying device 102 may output a visible light to a fiber port configured to receive an ophthalmic fiber probe. Different types of utilities may be supplied from the surgical utility supplying device 102 to different types of surgical implements 104 at the same time.

The utility may be output from a utility port 106 to the surgical utility connector 108 and be carried by a tube fiber or cable (referenced herein as cable 114) to the surgical implement 104. The surgical implements 104 may selectively be attached or detached from the utility ports 106 by the surgical utility connectors 108. For example, a surgical implement 104 may be detached from the surgical utility supplying device 102 by detaching the surgical utility connector 108 from the utility port 106. The surgical utility supplying device 102 may detect a connection of a surgical implement 104 and may allow the supply of utility to the surgical implement 104 after the connection. The surgical system 100 also may include a foot pedal 112 connected to the surgical utility supplying device 102 for controlling the dispensing of utility from the surgical system 100. For example, a user may control the dispensing of the utility by selectively pressing and releasing the foot pedal 112.

Figure 2:
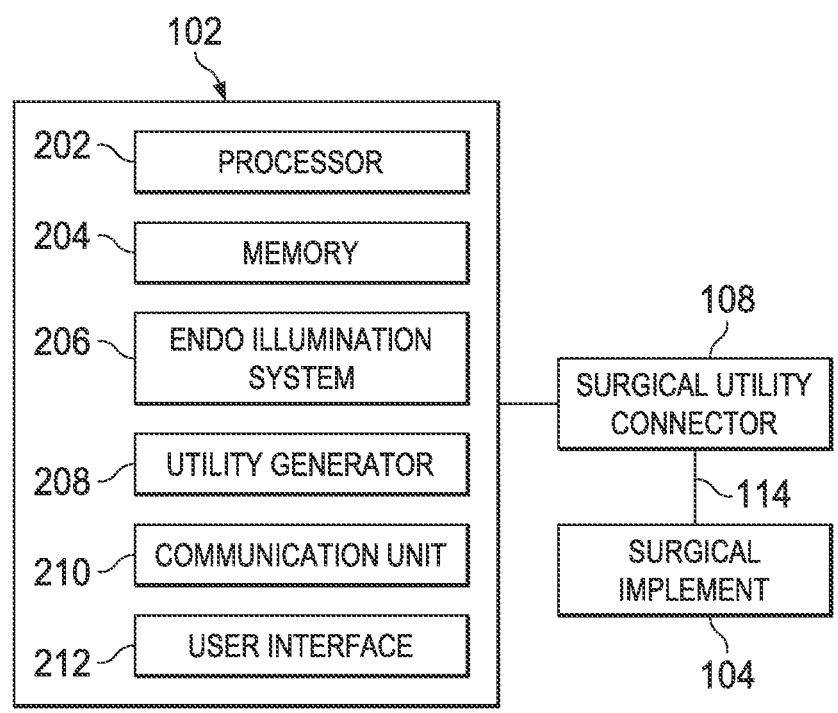
FIG. 2 illustrates a block diagram of a surgical system according to an aspect consistent with the principles of the present disclosure.

FIG. 2 illustrates a schematic diagram of an exemplary surgical utility supplying device, e.g., the surgical utility supplying device 102. The surgical utility supplying device 102 may include a processor 202 configured to perform calculation and determination for controlling various operations of the surgical utility supplying device 102. The processor 202 may receive various signal inputs and make various determinations based on the signal inputs. For example, the processor 202 may receive signals from an optical sensor configured to detect an amount of a light output to determine a coupling efficiency of a light beam into an optical fiber. The processor 202 also may control the display screen 110 to display various information regarding the operations of the surgical utility supplying device 102 to the user.

The surgical utility supplying device 102 may include a memory 204 configured to store information permanently or temporarily for various operations of the surgical utility supplying device 102. For example, the memory 204 may store programs that may be executed by the processor 202 to perform various functions of the surgical utility supplying device 102. The memory 204 also may store various data relating to operation history, user profile or preferences, various operation and surgical settings, and the like. Programs and information stored in the memory 204 may continuously be updated to provide customization and improvement in the operation of the surgical utility supplying device 102. The memory 204 also may include programs and information relating to operational parameters for coupling efficiency at different fiber ports.

The surgical utility supplying device 102 also may include an endo-illumination system 206. The endo-illumination system 206 may include optical components configured to couple a light beam into an ophthalmic fiber probe connected at a utility port, e.g., fiber port, of the surgical utility supplying device 102. In particular, the endo-illumination system 206 may include a collimator configured to receive light from a light source and collimate the light into a light beam, spectral filters configured to filter the light beam into desired spectrums, and a condenser configured to couple the light beam into an optical fiber of the ophthalmic fiber probe.

The surgical utility supplying device 102 may include a utility generator 208. The utility generator 208 may include motors, light emitting devices, pumps, and the like that may generate various utilities, such as illuminating light, imaging light, pressured liquid, compressed air, and the like. In an embodiment, the utility generator 208 may be connected to an external utility source to receive utility externally. For example, the utility generator 208 may be connected to a vacuum source or an air compressor to receive vacuum or compressed air. The utility generator 208 may supply various utilities to respective utility ports 106.

The surgical utility supplying device 102 may include a communication unit 210. The communication unit 210 may include various communication devices, such as Ethernet card, Wi-Fi (wireless) communication device, telephone device, digital I/O (Input and Output) ports or the like, that may allow the surgical utility supplying device to send and receive information to and from other devices. For example, the communication unit 210 may receive input from other surgical devices to coordinate a surgical operation. In another example, the communication unit 210 may transmit and receive messages or notifications, such as email, text, or other messages or notifications to a user's mobile device to notify certain information to the user.

The surgical utility supplying device 102 also may include a user interface 212. The user interface 212 may include user input devices, such as a keyboard, a touch screen, the foot pedal 112, a mouse, a microphone, or the like that allow a user to input instructions to the surgical utility supplying device 212. For example, the user may enter parameters for a utility and operate the foot pedal 112 to dispense the utility to the surgical implement 104. The user interface 212 also may include user output devices, such as a display screen 110, an audio speaker, LED (light-emitting diode) lights, or other visual or tactile signals that convey information to a user. For example, an audio speaker may emit an alarm when a coupling efficiency at a particular fiber port drops below a certain threshold during a surgical operation. Thus, the user interface 212 enables a user to interact with the surgical utility supplying device 102 during surgical operations.

Figure 3:
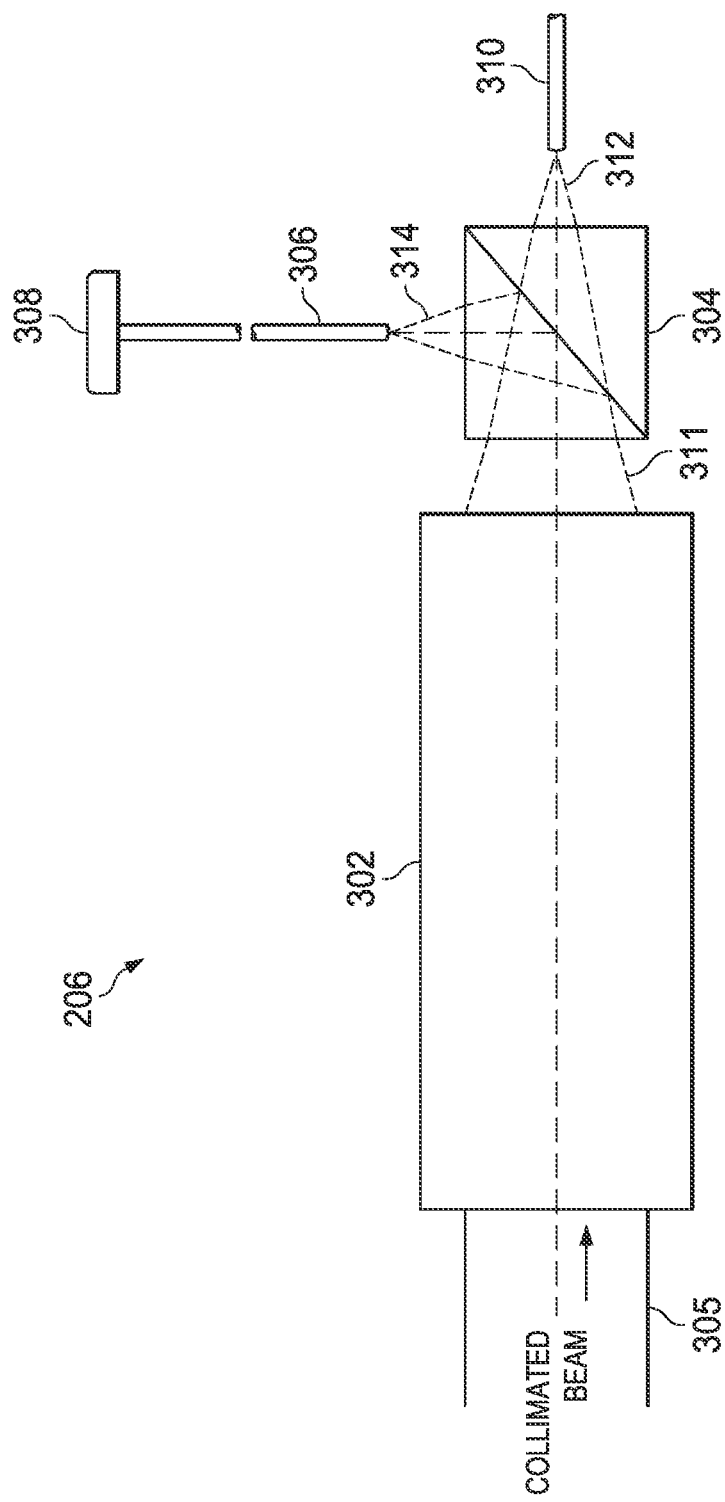
FIG. 3 illustrates a schematic diagram of an exemplary ophthalmic endo-illumination system according to an aspect consistent with the principles of the present disclosure.

FIG. 3 illustrates a schematic diagram of an ophthalmic endo-illumination system 206 according to one embodiment. The ophthalmic endo-illumination system 206 may include a condenser 302 configured to receive a light beam 305. In particular, a light source (not shown in FIG. 3) may produce a light which may be collimated into a light beam 305 by a collimator (not shown). The condenser 302 may receive the light beam 305 and couple the light beam 305 into an optical fiber 310 of a surgical implement 104, e.g., an ophthalmic fiber probe, connected to the utility port 106, e.g., a fiber port.

The ophthalmic endo-illumination system 206 may include a beam splitter 304 disposed between the condenser 302 and the optical fiber 310 and configured to split a light beam 311 from the condenser 302 into a first beam 312 and a second beam 314. For example, the beam splitter 304 may receive the coupled light beam from the condenser 302 and transmit a portion of the light beam while reflecting a portion of the light beam. As such, the first beam 312 is transmitted to continue to reach the optical fiber 310. Thus, the first beam 312 may be coupled into the optical fiber 310. The second beam is reflected or diverted in a different direction, e.g., a perpendicular direction from the first beam, toward a monitoring fiber 306. Thus, the second beam may be coupled into the monitoring fiber 306.

The beam splitter 304 may be a beam splitter cube or any other optical device configured to receive a light beam and split the light beam into two different light beams. The beam splitter 304 may receive the light beam and divert a portion of the light beam, e.g., between 0.8% to 1.5% of the beam power, into the second beam 314. The main portion of the light beam, e.g., between 99.2% to 97.5% of the beam power, may be transmitted straight into the optical fiber 310 of the ophthalmic fiber probe. In an exemplary embodiment, the optical fiber 310 is a 25 μm (micrometer) core and 0.26 Numerical Aperture (NA) multi-mode optical fiber with a 7 μm toleranced core diameter. In other embodiments, optical fibers with different diameters or sizes may be used.

The second beam 314 may be focused into the monitoring fiber 306. The monitoring fiber 306 may have a smaller core diameter than that of the optical fiber 310. For example, one exemplary embodiment of a monitoring fiber 306 is a 4.3 μm core and 0.12 NA single-mode optical fiber. The monitoring fiber 306 may receive the second light beam 314 at a proximal end. The second light beam 314 may propagate within the monitoring fiber 306 and exit at a distal end of the monitoring fiber 306. The monitoring fiber 306 may have a length of several inches such that any light modes from the cladding of the monitoring fiber 306 are substantially eliminated. An optical sensor 308 may be provided at the distal end of the monitoring fiber 306 to detect the power or amount of the second beam 314 at the distal end.

The beam splitter 304, the proximal end of the monitoring fiber 306, and the proximal end of the optical fiber 310 may be arranged in a particular manner such that the first beam and the second beam are parfocal except that the second beam 314 is folded. For example, if the folded second beam 314 were unfolded, the second beam 314 and the first beam 312 may coincide in space. In particular, if unfolded, the second beam 314 and the position of the entrance aperture of the monitoring fiber 306 may coincide in space with the first beam 312 and the position of the entrance aperture of the optical fiber 310. Thus, a coupling position and/or coupling efficiency of the first beam 312 at the proximal end of the optical fiber 310 may directly correspond to the coupling position and/or coupling efficiency of the second beam 314 at the proximal end of the monitoring fiber 306. Therefore, by monitoring the amount of the second beam 314 at the monitoring fiber 306, the coupling efficiency of the first beam 312 at the optical fiber 310 may be determined.

Figure 4:
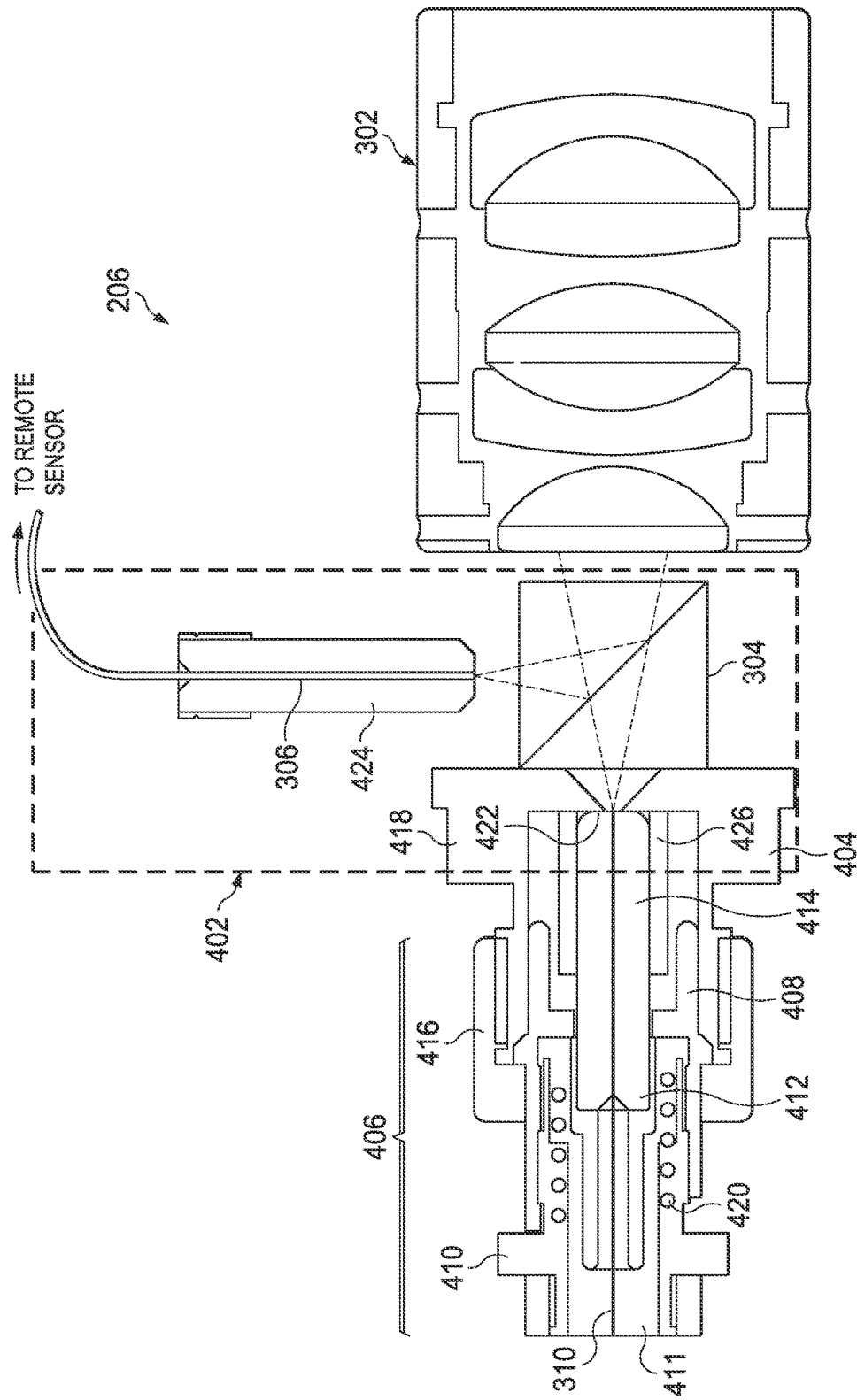
FIG. 4 illustrates a detailed schematic diagram of an exemplary ophthalmic endo-illumination system according to an aspect consistent with the principles of the present disclosure.

FIG. 4 illustrates a detailed schematic diagram of an exemplary ophthalmic endo-illumination system according to an embodiment. As shown in FIG. 4, the ophthalmic endo-illumination system 206 may include the condenser 302 which may include one or more optical lenses or other optical components configured to focus a light beam. The ophthalmic endo-illumination system 206 may include a fiber port 404, which may be one of the utility ports 106, as shown in FIG. 1. The fiber port 404 may be configured to receive a fiber connector 406, e.g., the utility connector 108 as shown in FIG. 1. The fiber connector 406 may connect the optical fiber 310 to the fiber port 404. The optical fiber 310 may extend within the cable 114 (FIG. 1) and may guide a light beam to the surgical implement 104 (FIG. 1), such as an endo-illuminator probe. The fiber connector 406 may be removable from the fiber port 404 to disconnect the endo-illuminator probe from the ophthalmic endo-illumination system 206.

The fiber connector 406 may include a front body 408 and a rear body 410. A channel 411 may be formed through each of the front body 408 and the rear body 410. A ferrule 414 may be provided within the channel 411. The optical fiber 310 may be accommodated in the ferrule 414. The fiber port 404 may include a cylindrical recess configured to receive the front body 408 of the fiber connector 406. The cylindrical recess may be formed by a cylindrical wall 418 which may surround a portion of the front body 408 of the fiber connector 406 when the fiber connector 406 is connected to the fiber port 404.

The fiber connector 406 may include a nut 416 including female thread on its inner surface which may interact with male threads provided on an outer surface of the cylindrical wall 418 of the fiber port 404 to secure the fiber connector 406 at the fiber port 404. The cylindrical recess of the fiber port 404 may include an inner end surface 422. An opening may be formed through the inner end surface 422 through which a light beam may project to be coupled into the optical fiber 310. When the fiber connector 406 is connected to the fiber port 404, a proximal end surface of the ferrule 412 may abut against the inner end surface 422 such that a proximal end surface of the optical fiber 310 is positioned at the opening of the inner end surface 422. A sleeve 426 may be provided to accommodate and to position the ferrule 412, such that the proximal end of the optical fiber 310 is precisely positioned at the opening of the inner end surface 422. The sleeve 426 may be formed with a material that is not easily deformed or change shape, such that the ferrule 412 and the optical fiber 310 may be positioned precisely at the opening of the inner end surface 422. A spring 420 may be provided in the fiber connector 406 to exert a biasing force on the ferrule 412 to tightly abut the ferrule 412 against the inner end surface 422 of the fiber port 404.

The beam splitter 304 may be provided between the condenser 302 and the fiber port 404. The beam splitter 304 may abut against the fiber port 404. In an embodiment, a space may be provided between the beam splitter 304 and the fiber port 404. The monitoring fiber 306 may be provided in a ferrule 424. The ferrule 424 may be positioned above the beam splitter 304. As noted above, the ferrule 424, the fiber port 404, and the beam splitter 304 may be positioned in a manner that results in a parfocal relationship between a transmitted light beam and a reflected light beam from the beam splitter 304. As such, a deviation from a coupling position at the fiber port 404 corresponds to a deviation from a coupling position at the monitoring fiber 306.

The monitoring fiber 306 in the ferrule 424, the fiber port 404, and the beam splitter 304 may be provided in an athermalized assembly 402, shown as a dashed line area in FIG. 4, within which the optical characteristics of the assembly, such as the parfocal relationship, remain the same in changing temperatures. For example, the athermalized assembly may maintain the same optical characteristics between 10° C. and 35° C. In an embodiment, the athermalized assembly 402 may include an optical coupling efficiency detection assembly, as described below.

In some embodiments, the condenser 302 may be included in the athermalized assembly 402. The athermalized assembly 402 may include a collection of optical components that coordinate to minimize the overall effect caused by temperature changes. For example, thermal expansion of optical components, such as glass lenses or metal housings, may cause the focal length of the focused beam to increase. Further, the glass refractive index of lenses also may increase with temperature to have greater optical power and may cause the focal length of focused beam to decrease. By selecting the glass types, lens radii of curvature, lens center thickness, etc. of the optical components to be included in the athermalized assembly 402, the effects caused by temperature changes may cancel each other out to maintain the same overall optical characteristics in the system.

During an assembly process of the ophthalmic endo-illumination system, it is important to rigidly or fixedly secure the different components in order to maintain the parfocal relationship between the transmitted and reflected beam paths. Otherwise, the relative positions of the optical components may move during the assembly process, and a proper parfocal alignment between the fiber port 404, the beam splitter 304, and the ferrule 424 is important for a successful operation of the system. The optical coupling efficiency detection assembly may include components that maintain the parfocal alignment during the assembly process.

Figure 5A:
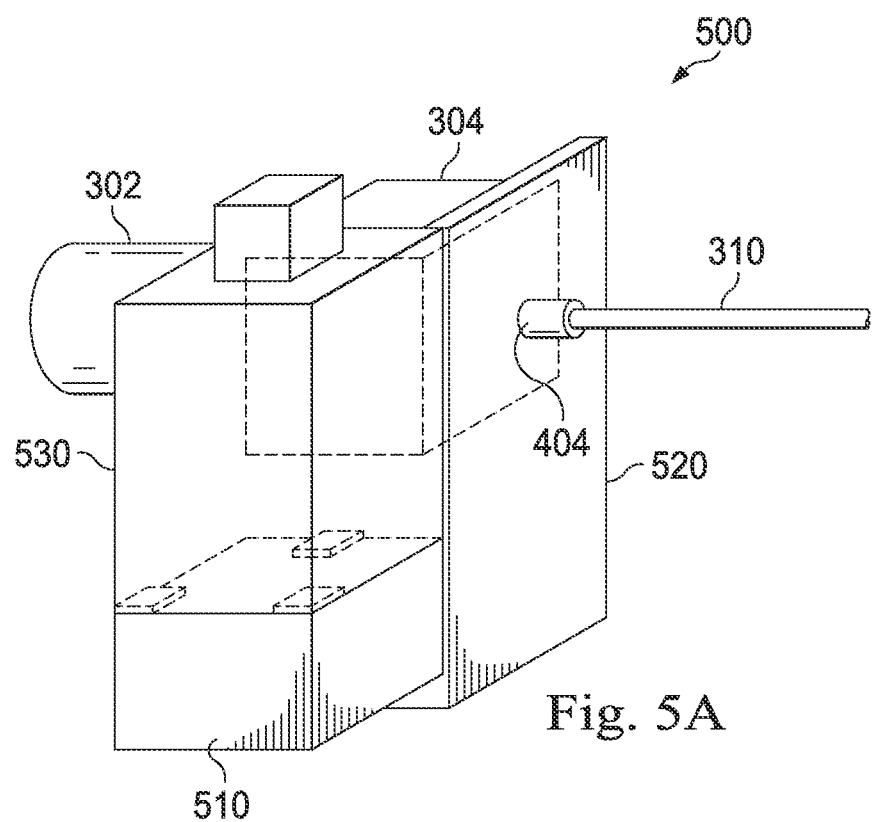
FIG. 5A illustrates a schematic diagram of an optical coupling efficiency detection assembly of an ophthalmic endo-illumination system according to an aspect consistent with the principles of the present disclosure.

FIG. 5A illustrates a schematic diagram of an optical coupling efficiency detection assembly 500 of an ophthalmic endo-illumination system according to an embodiment. The optical coupling efficiency detection assembly 500 may include a first housing 520 and a second housing 530 attached to the first housing 520 via an attachment block 510. The first housing 520 may include the beam splitter 304 and the fiber port 404 configured to receive an optical fiber 310. The condenser 302 may direct a light beam through the beam splitter 304 and focus the light beam into the optical fiber 310 positioned at the fiber port 404.

The second housing 530 may include the monitoring fiber 306 (not shown). The attachment block 510 may attach to the first housing 520 at one side and to the second housing 530 at another side. As such, the attachment block 510 may attach the first housing 520 to the second housing 530 and may maintain relative positions between the first housing 520 and the second housing 530. The attachment block 510 may be attached to the first and the second housings 520 and 530, respectively, by bonding adhesive or any other fastening means to immobilize the first housing 520 relative to the second housing 530. The first housing 520, the second housing 530, and the attachment block 510 may be formed with precision materials that are not easily deformed or altered, such as precision metal or the like. For example, the first housing 520, the second housing 530, and the attachment block 510 may be formed of stainless steel, titanium, aluminum, or others.

Figure 5B:
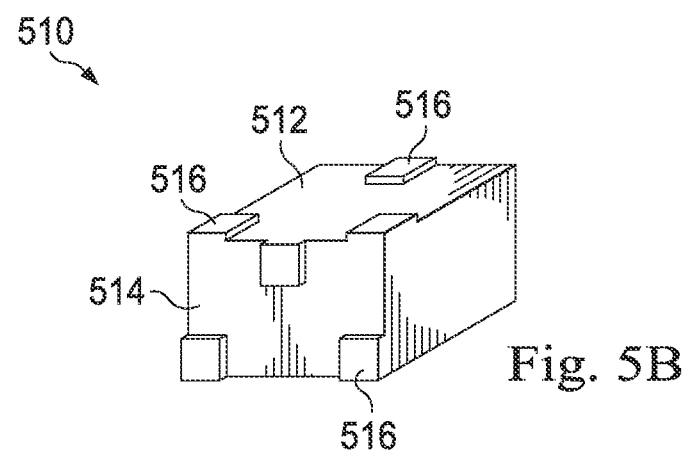
FIG. 5B illustrates a schematic diagram of an attachment block according to an aspect consistent with the principles of the present disclosure.

FIG. 5B illustrates a schematic diagram of an attachment block according to an embodiment. The attachment block 510 may include a first attachment surface 512 configured to be bonded to the first housing 520 and a second attachment surface 514 configured to be bonded to the second housing 530. Here, the attachment block includes a plurality of planar sides forming the first and second attachment surfaces 512, 514. The first and second attachment surfaces 512, 514 in this embodiment are aligned along perpendicular planes and are adjacent each other, such that the surfaces together form a 90 degree angle. Abutment pads 516 are provided on the first attachment surface 512 and the second attachment surface 514, respectively. In particular, abutment pads 516 are disposed along a perimeter portion of each of the first attachment surface 512 and the second attachment surface 514. The abutment pads 516 may have flat top surfaces configured to contact a bottom surface of the second housing 530 or a side surface of the first housing 520 when the attachment block 510 is attached to the first housing 520 or the second housing 530. As shown in FIG. 5B, three abutment pads 516 are provided in each of the first attachment surface 512 and the second attachment surface 514. Three pads provide three spaced contact points within a single plane. Accordingly, three pads can improve stability and reduce the chance of rocking that may occur when more than three pads are used. However, any number of abutment pads 516 may be provided as appropriate.

The abutment pads 516 may be rigid, substantially incompressible spacers that offset or space the attachment block 510 from the first and second housings 520, 530. The abutment pads 516 may have a rectangular, square, or other shape and may protrude from the attachment surfaces. Bonding adhesives may be applied on the first attachment surface 512 and the second attachment surface 514. The bonding adhesives may be applied between and surrounded by the abutment pads 516. A height of the abutment pads 516 on the first attachment surface 512 may correspond to a thickness of the bonding adhesive provided on the first attachment surface 512 when the first attachment surface 512 is attached to the side surface of the first housing 520. Similarly, a height of the abutment pads 516 on the second attachment surface 514 may correspond to a thickness of the bonding adhesive provided on the second attachment surface 514 when the second attachment surface 514 is attached to the bottom surface of the second housing 530. As such, the abutment pads 516 may provide precise contact, spacing and positioning between the attachment block 510 and the first and the second housings 520 and 530, respectively. The abutment pads 516 may allow the relative positions of the first housing 520 and the second housing 530 to be maintained during the assembly and attachment process.

Figure 6:
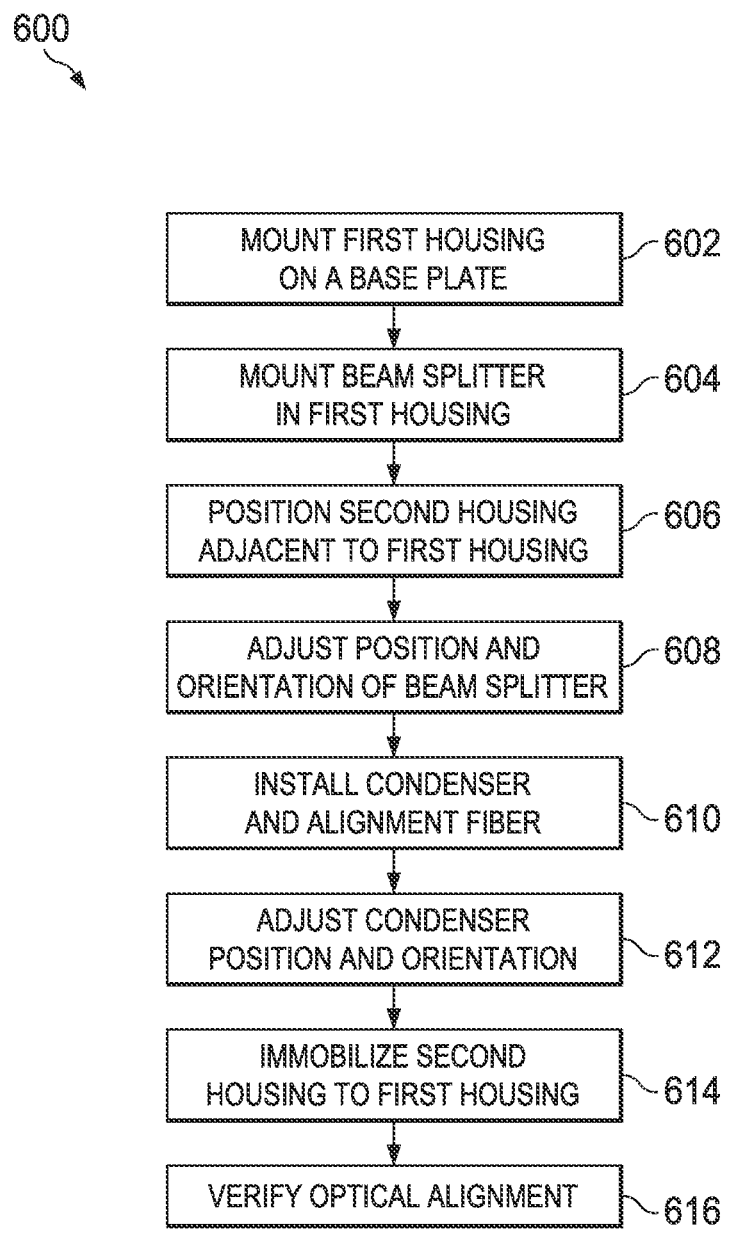
FIG. 6 is a flow chart illustrating an assembly process for an optical coupling efficiency detection assembly according to an aspect consistent with the principles of the present disclosure.
Figure 7A:
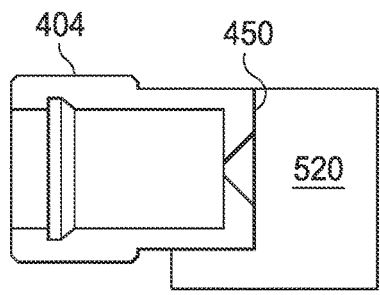
FIGS. 7A-7H are schematic diagrams illustrating various phases in an assembly process for an optical coupling efficiency detection assembly according to an aspect consistent with the principles of the present disclosure.
Figure 7B:
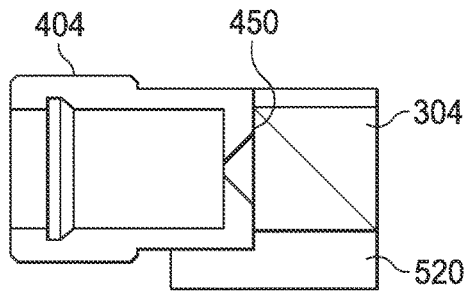

FIG. 6 is a flow chart illustrating an assembly process 600 for an optical coupling efficiency detection assembly 500 according to an exemplary embodiment. At 602, the first housing 520 with the fiber port 404, as shown in FIG. 7A, may be mounted on a base plate (not shown). At 604, the beam splitter 304 may be mounted onto the first housing 520. In particular, the beam splitter 304 may be positioned squarely against a planar reference surface 450 of the fiber port 404. In an embodiment, the beam splitter 304 may be positioned squarely against a lateral planar reference surface of the first housing 520.

Figure 7C:
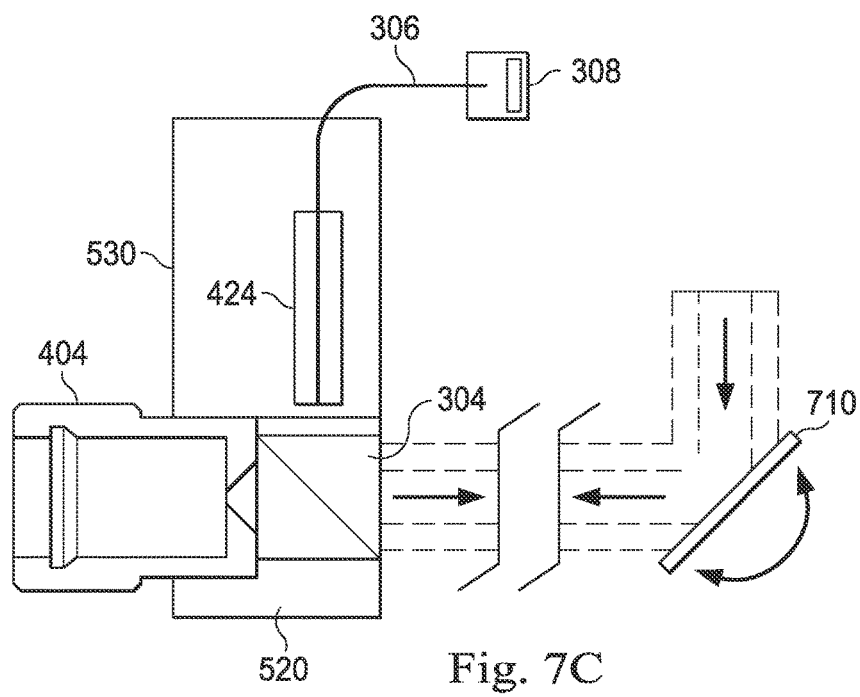

At 606, the second housing 530 may be positioned adjacent to the first housing 520, as shown in FIG. 7C. The second housing 530 may include the ferrule 424 and the monitoring fiber 306. A proximal end of the monitoring fiber 306 may be positioned relative to the beam splitter 304. In an embodiment, micro-positioning elements, such as pico motors, may be used to position the second housing 530 to provide precise movements. A distal end of the monitoring fiber 306 may be connected to an optical sensor 308. In an embodiment, the monitoring fiber 306 may be a 0.12 NA fiber with 4.3 µm core diameter.

At 608, a collimated laser beam, such as a 543.5 nm (nanometer) HeNe laser beam, may be directed at the beam splitter 304, as shown in FIG. 7C. The positional and angular orientation of the laser beam may be adjusted by a steering mirror 710, such that the laser beam is laterally centered on the fiber port 404 and retro-reflected off of a first surface of the beam splitter 304, as shown in FIG. 7C.

Figure 7D:
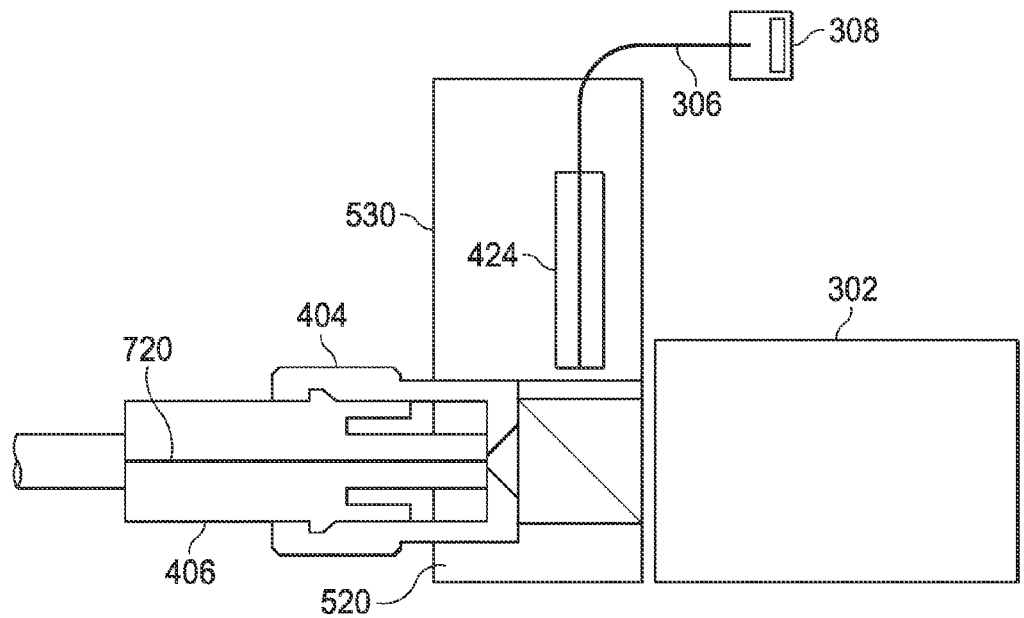

At 610, the condenser 302 is provided between the steering mirror 710 and the beam splitter 304, as shown in FIG. 7D. The condenser 302 may be attached to an x-y-z translation stage that is configured to adjust the position, tilt, and orientation of the condenser 302. An alignment fiber 720 may be installed at the fiber port 404, as shown in FIG. 7D. The alignment fiber 720 may have a tighter coupling tolerance than fibers 310 that are normally used. For example, the alignment fiber 720 may have a smaller core of 4.3 µm.

Figure 7E:
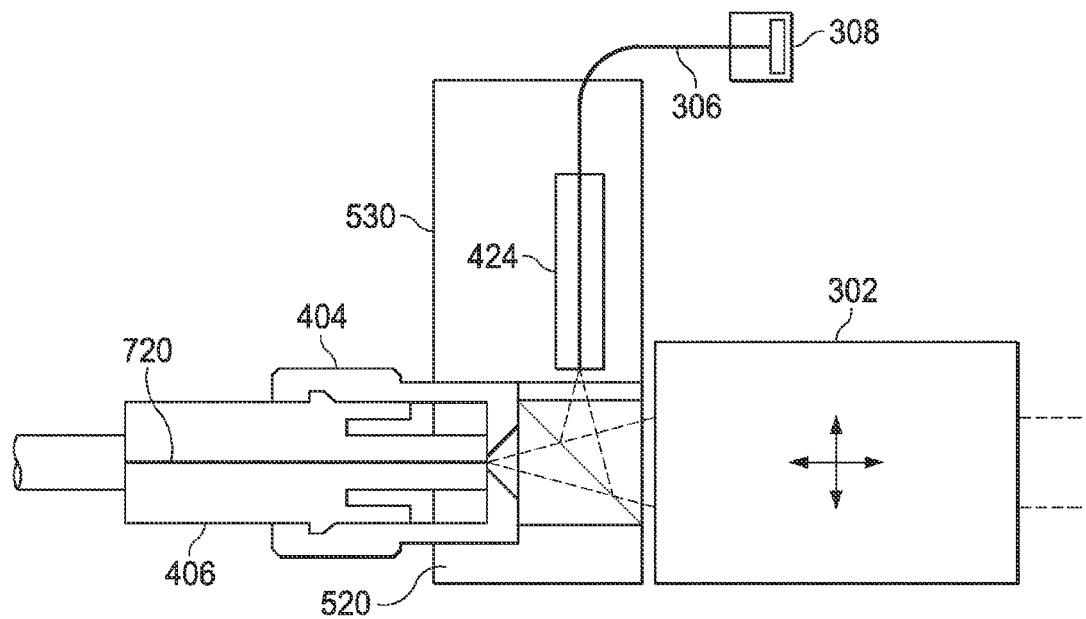

At 612, the position, tilt, and orientation of the condenser 302 may be adjusted to optimize the coupling efficiency into the alignment fiber 720, as shown in FIG. 7E.

In particular, the x-y-z translation stage supporting the condenser 302 may be adjusted to change the position of the condenser 302 until the coupling efficiency into the alignment fiber 720 is optimized. For example, the light intensity received by the alignment fiber 720 may be detected. The coupling efficiency into the alignment fiber 720 is optimized when the light intensity received by the alignment fiber 720 is maximized. In particular, the position of the condenser 302 may be adjusted such that the cone of the focused beam is angularly centered about the optical axis of the alignment fiber 720. The x-y-z translation stage may translate the condenser 302 in x and y directions and axially translate the condenser 302 in the z direction to achieve optimal coupling efficiency. 610 and 612 may be repeated until the optimal coupling efficiency into the alignment fiber 720 is achieved.

In another embodiment, a $\theta\phi z$ translation stage may be provided to support the condenser 302. The $\theta\phi z$ translation stage may provide compound tilt of the condenser 302 as well as an axial linear adjustment of the condenser 302. When the pivot point of the condenser $\theta\phi z$ translation stage is in a different location than the principal plane of the condenser 302, then the compound tilt of the condenser 302 may cause a change in the lateral (x and y) position of the focused beam spot. Therefore, the condenser $\theta\phi z$ stage may provide an xyz adjustment of the focused beam spot relative to the fixed fiber, similar to that of the condenser xyz stage.

Figure 7F:
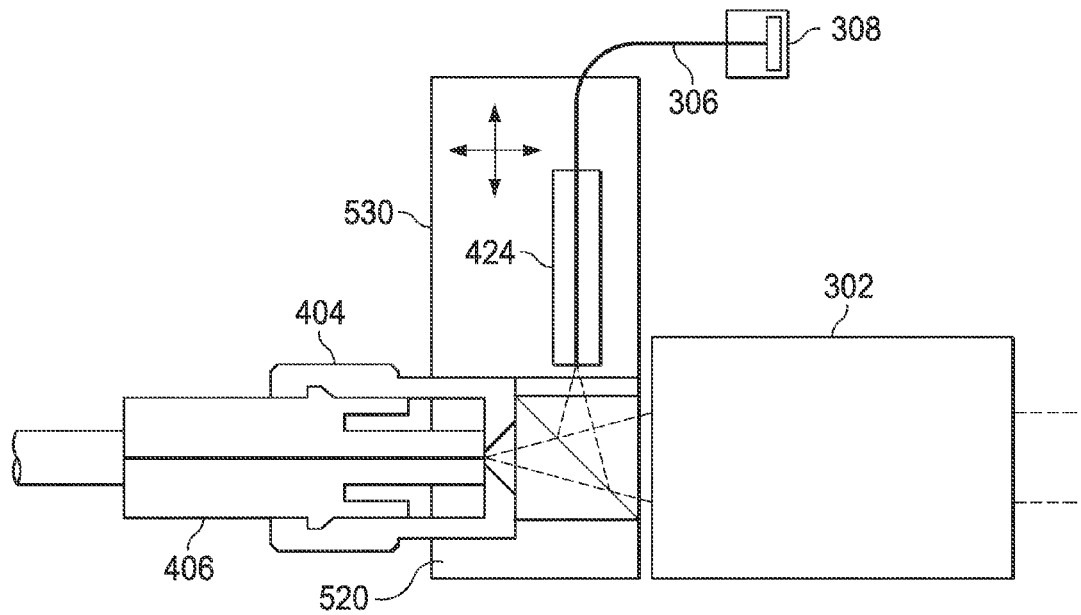

At 614, the position of the second housing 530 may be adjusted to optimize the coupling efficiency into the monitoring fiber 306, as shown in FIG. 7F. For example, the light intensity received by the monitoring fiber 306 may be detected by optical sensor 308. The coupling efficiency into the monitoring fiber 306 is optimized when the light intensity received by the optical sensor 308 is maximized.

Figure 7G:
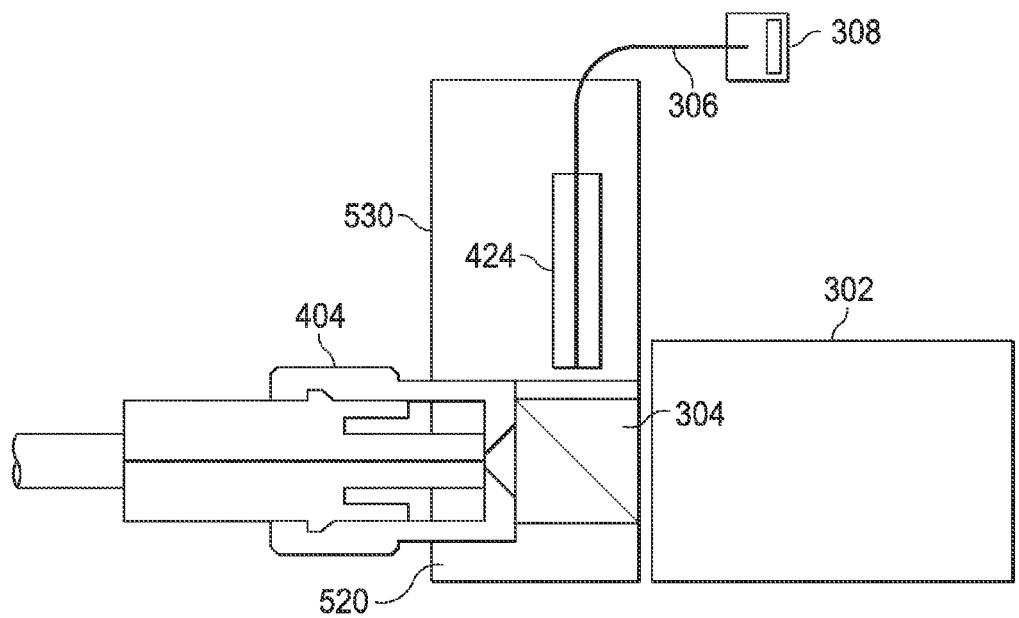
Figure 7H:
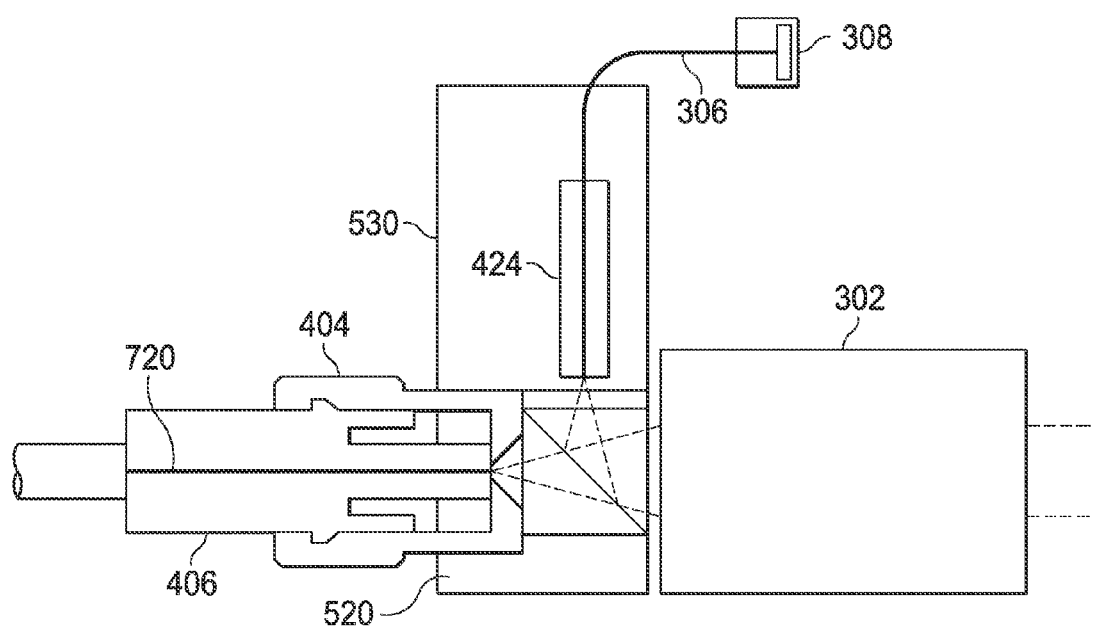

At 614, the first housing 520 may be permanently immobilized with respect to second housing 530 in an attachment process, as shown in FIG. 7G. As such, the attachment process may maintain a permanent parfocal relationship between the fiber port 404, the beam splitter 304, and the ferrule 424. At 616, the parfocal relationship of the parts are verified again after the immobilization to confirm that their relative positions are maintained during the attachment process, as shown in FIG. 7H. For example, the laser beam is introduced into the beam splitter and the optical coupling efficiencies at both the monitoring fiber 306 and at the alignment fiber 720 are measured to confirm they are still at optimal levels.

Figure 8A:
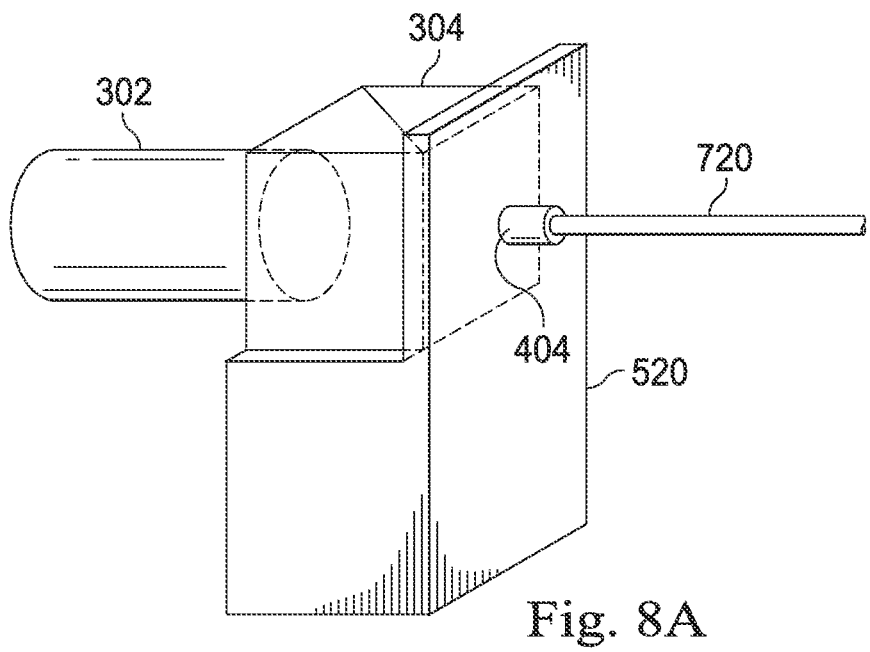
FIGS. 8A-8F are schematic diagrams illustrating various phases in an attachment process for an optical coupling efficiency detection according to an aspect consistent with the principles of the present disclosure.
Figure 8B:
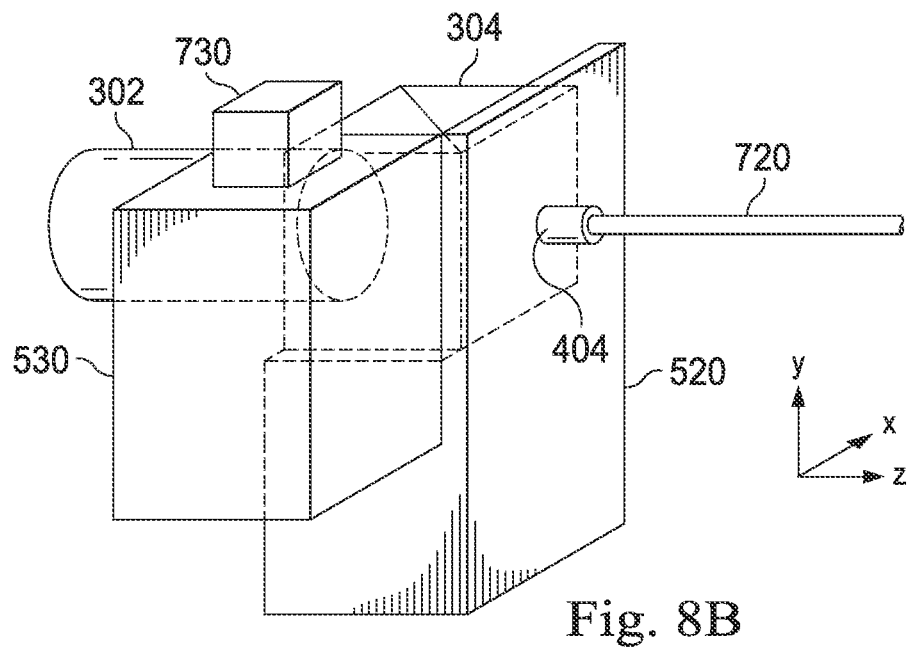
Figure 8C:
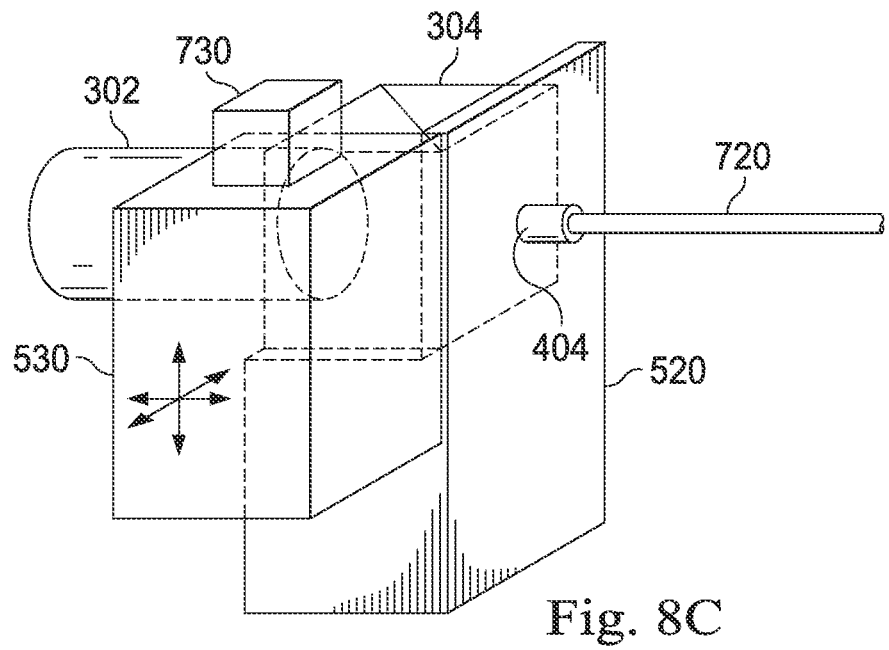

The attachment process for permanently immobilizing the various parts at 614 is further illustrated in FIGS. 8A-8F. As shown in FIG. 8A, the position of the condenser 302 is adjusted relative to the beam splitter 304 and the alignment fiber 720 to optimize the optical efficiency into the alignment fiber 720. As shown in FIG. 8B, the second housing 530 then may be positioned relative to the beam splitter 304. The second housing 530 may include the ferrule 424 that supports the monitoring fiber 306. The second housing 530 may include an attachment portion 730, such as a vacuum chuck, configured to attach to an adaptor of a precision adjustable x-y-z translation stage. As shown in FIG. 8C, the position of the second housing 530 may be adjusted by the precision adjustable x-y-z translation stage to position the monitoring fiber 306 relative to the beam splitter 304, as described in 614.

Figure 8D:
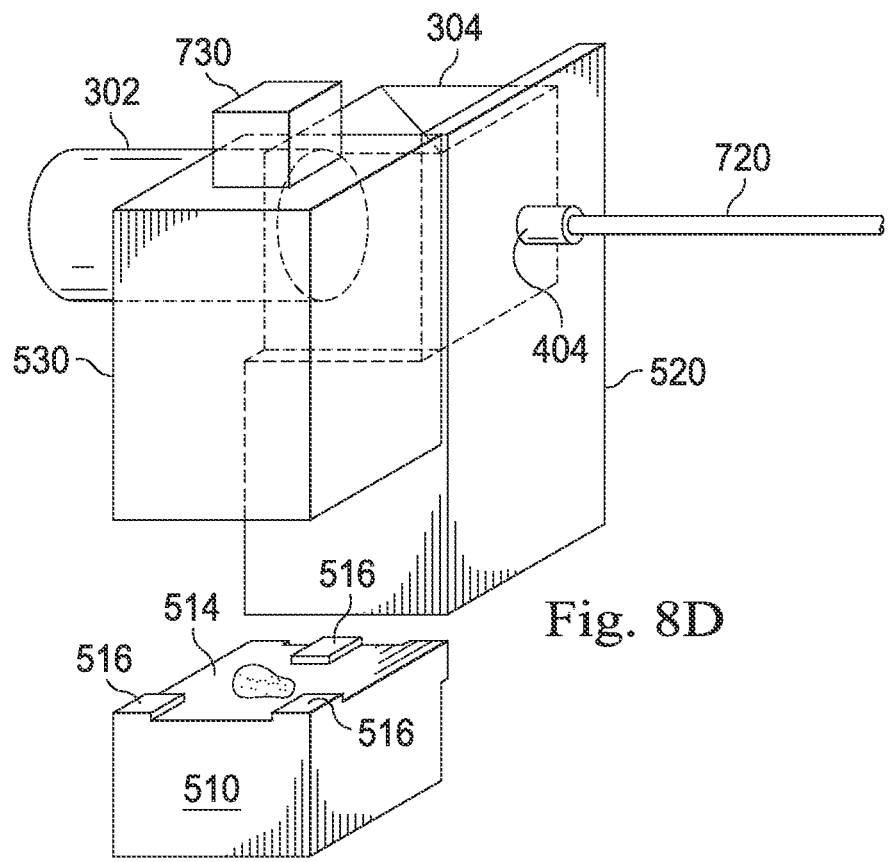

As shown in FIG. 8D, the attachment block 510 configured to attach the first housing 520 to the second housing 530 may be prepared. In particular, bonding adhesives may be applied or titrated onto the attachment surfaces 512 and 514. In an embodiment, the bonding adhesive may be, for example, a 30-minute cure, viscous adhesive (other adhesive types and cure times are also possible). A height or thickness of the bonding adhesive on the attachment surfaces 512 and 514 may be slightly greater than a height of the abutment pads 516. In some methods, the bonding adhesive is not applied to the abutment pads.

Figure 8E:
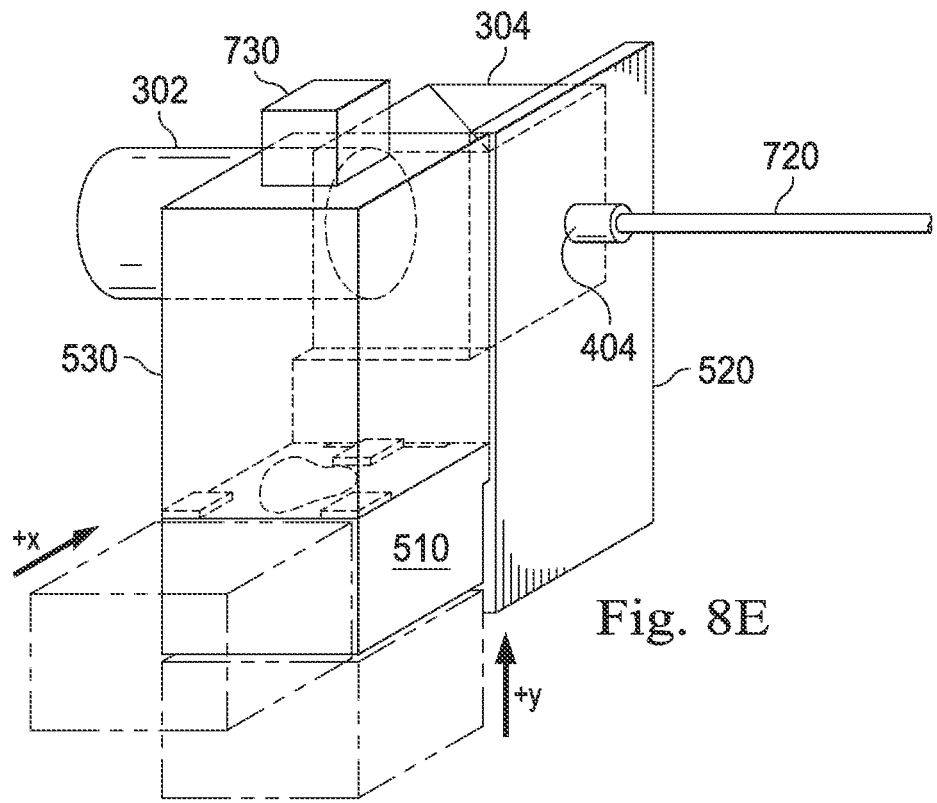

As shown in FIG. 8E, the attachment block 510 may be attached to the first housing 520 and the second housing 530. In particular, a top portion of the attachment block 510 may interface with a bottom surface of the second housing 530 and a side portion of the attachment block 510 may interface with a side surface of the first housing 520. The bonding adhesive on the attachment surface 514 of the attachment block 510 may be titrated in a particular amount and shape, such that when the top portion of the attachment block 510 comes into contact with the bottom surface of the second housing 530, the bonding adhesive is compressed by the bottom surface of the second housing 530 and the bonding adhesive fills the gap between the attachment surface 514 and the bottom surface of the second housing 530, without touching the abutment pads 516 on the attachment surface 514.

Similarly, the bonding adhesive on the attachment surface 512 of the attachment block 510 may be titrated in a particular amount and shape, such that when the side portion of the attachment block 510 comes into contact with the side surface of the first housing 520, the bonding adhesive is compressed by the side surface of the first housing 520 and the bonding adhesive fills the gap between the attachment surface 512 and the side surface of the first housing 520, without touching the abutment pads 516 on the attachment surface 512.

Because the bonding adhesives do not interfere with the abutment pads 516, the abutment pads 516 may have direct and precise contact with the first housing 520 and the second housing 530, respectively. Accordingly, the attachment surface is precisely spaced from the first housing to accommodate the bonding adhesive without affecting the relative positions of the attachment block and the housing. The attachment block 510 may be adjusted by a precision x-y-z translation stage. For example, the x-y-z translation stage may move in a +X direction to move the attachment block 510 toward the side surface of the first housings and may move in a +Y direction to move the attachment block 510 up toward the bottom surface of the second housing 530.

In particular, the x-y-z translation stage may be provided with biasing members, such as springs that provide a slight biasing force to press the attachment block 510 onto both the first and the second housings 520 and 530. For example, the biasing members of the x-y-z translation stage may supply a force slightly larger than zero in the +X direction to press the attachment block 510 toward the first housing 520, such that the abutment pads 516 on the attachment surface 512 tightly abut the first housing 520, but without moving the first housing 520 out of its alignment. Similarly, the biasing members of the x-y-z translation stage may supply a force slightly larger than the weight of the attachment block 510 in the +Y direction to press the attachment block 510 toward the second housing 530, such that the abutment pads 516 on the attachment surface 514 tightly abut the second housing 530, but without moving the second housing 530 out of its alignment.

During the curing process of the bonding adhesives, the biasing members of the x-y-z translation stage may continue to support and gently press the attachment block 510 onto the first and the second housings 520 and 530. In an embodiment, the bonding adhesive may have a thermal expansion coefficient similar to or slightly less than the materials of the first and the second housings 520 and 530 and the attachment block 510. As such, when the bonding adhesive shrinks during the curing process, the bonding adhesive may pull the attachment block 510 tightly against the first and the second housings 520 and 530, respectively. Since the abutment pads may be rigid and substantially incompressible, the spacing between the attachment surface and the housing may remain unchanged. Further, this bonding adhesive may continue to exert this pulling force after the assembly and curing process during the normal operation of the optical coupling efficiency detection assembly.

Further, during the curing process, the optical coupling efficiency at the alignment fiber 720 and at the monitoring fiber 306 may continuously be monitored. As such, the positions of the first housing 520 and the second housing 530 may be adjusted during the curing process, as appropriate, to maintain the parfocal relationship among the optical components.

Figure 8F:
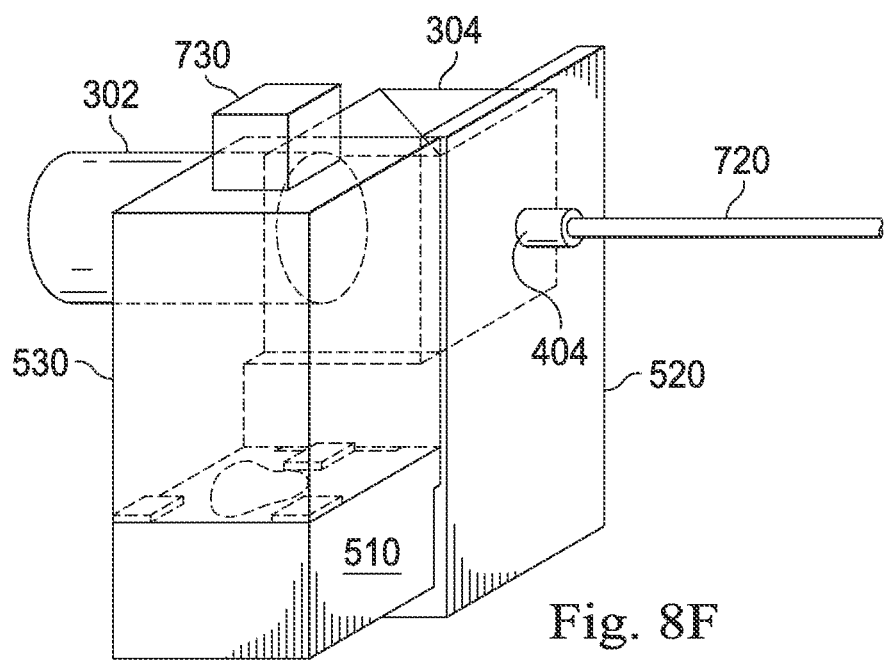

As shown in FIG. 8F, after the bonding adhesive is cured, the biasing members may gently be removed to release the attachment block 510. In another embodiment, the biasing members may be left in situ permanently. Further, second housing 530 may be released from the x-y-z translation stage by releasing the attachment portion 730 from the adaptor of the precision adjustable x-y-z translation stage.

Accordingly, the above embodiments provide an optical coupling efficiency detection assembly including an attachment block that allows precise attachment of the first housing to the second housing. Further, an assembly method is provided that combines the ability for precision adjustment of the housings and the ability to maintain precise contacts between the housings and the attachment block during the optical alignment process. In particular, the assembly block may include abutment pads that provide precise and continuous contacts between the housings and the attachment block during the curing process of the bonding adhesive. Thus, the parfocal relationship among optical components in the optical coupling efficiency detection assembly may be maintained during the assembly and curing process.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. An assembly method for an optical coupling efficiency detection assembly, the assembly method comprising:
    providing a beam splitter and a fiber port in a first housing;
    providing a ferrule enclosing a monitoring fiber in a second housing;
    rigidly attaching the first housing to a planar first side of an attachment block; and
    rigidly attaching the second housing to a planar second side of the attachment k that is adjacent to the first side of the attachment block to establish a parfocal arrangement among the beam splitter; the fiber port, and the ferrule;
    positioning the second housing relative to the first housing to form the parfocal arrangement; and
    immobilizing the second housing relative to the first housing by bonding the attachment block to the first housing and the second housing;
    wherein the positioning comprises:
        directing a light beam from a condenser into the beam splitter to split and couple the light beam simultaneously into an alignment fiber installed at the fiber port and the monitoring fiber at the ferrule;
        adjusting a position of the condenser to align the light beam with the beam splitter and the fiber port;
        detecting a coupling efficiency at the monitoring fiber; and
        adjusting a position of the second housing to optimize the coupling efficiency at the monitoring fiber.

2. The assembly method of claim 1, wherein the immobilizing comprises:
    applying a bonding adhesive on a first attachment surface forming a part of the planar first side of the attachment block;
    applying the bonding adhesive on a second attachment surface forming a part of the planar second side of the attachment block; and
    positioning the first attachment surface to the first housing and the second attachment surface to the second housing to bond the attachment block to the first housing and the second housing.

3. The assembly method of claim 2, further comprising:
    applying a first biasing force on the attachment block toward the first housing during a curing process of the bonding adhesive; and
    applying a second biasing force slightly greater than a weight of the attachment block on the attachment block toward the second housing during the curing process of the bonding adhesive.

4. The assembly method of claim 2, wherein the bonding adhesive has a thermal expansion coefficient equal to or less than that of the first housing, the second housing, and the attachment block.

5. The assembly method of claim 2,
wherein first abutment pads are disposed along a perimeter portion of the first attachment surface and second abutment pads are disposed along a perimeter portion of the second attachment surface, and
wherein the bonding adhesive is titrated on a center portion of the first attachment surface and a center portion of the second attachment surface, such that the bonding adhesive does not interfere with the first and the second abutment pads.

6. The assembly method of claim 1, wherein each of the first housing, the second housing, and the attachment block comprises precision metal material.

7. An assembly method for an optical coupling efficiency detection assembly, the assembly method comprising:
providing a beam splitter and a fiber port in a first housing;
providing a ferrule enclosing a monitoring fiber in a second housing;
rigidly attaching the first housing to a planar first side of an attachment block; and
rigidly attaching the second housing to a planar second side of the attachment block that is adjacent to the first side of the attachment block to establish a parfocal arrangement among the beam splitter, the fiber port, and the ferrule:
positioning the second housing relative to the first housing to form the parfocal arrangement; and
immobilizing the second housing relative to the first housing by bonding the attachment block to the first housing and the second housing;
wherein the immobilizing comprises:
applying a bonding adhesive on a first attachment surface forming a part of the planar first side of the attachment block;
applying the bonding adhesive on a second attachment surface forming a part of the planar second side of the attachment block; and
positioning the first attachment surface to the first housing and the second attachment surface to the second housing to bond the attachment block to the first housing and the second housing;
wherein first abutment pads disposed on the first attachment surface contact the first housing and second abutment pads disposed on the second attachment surface contact the second housing when the attachment block is attached to the first housing and the second housing.

8. The assembly method of claim 7,
wherein the first abutment pads are disposed along a perimeter portion of the first attachment surface and the second abutment pads are disposed along a perimeter portion of the second attachment surface, and
wherein the bonding adhesive is titrated on a center portion of the first attachment surface and a center portion of the second attachment surface, such that the bonding adhesive does not interfere with the first and the second abutment pads.

9. The assembly method of claim 7, further comprising:
applying a first biasing force on the attachment block toward the first housing during a curing process of the bonding adhesive; and
applying a second biasing force slightly greater than a weight of the attachment block on the attachment block toward the second housing during the curing process of the bonding adhesive.

10. The assembly method of claim 7, wherein the bonding adhesive has a thermal expansion coefficient equal to or less than that of the first housing, the second housing, and the attachment block.

11. The assembly method of claim 7, wherein each of the first housing, the second housing, and the attachment block comprises precision metal material.

12. An assembly method for an optical coupling efficiency detection assembly, the assembly method comprising:
providing a beam splitter and a fiber port in a first housing;
providing a ferrule enclosing a monitoring fiber in a second housing;
rigidly attaching the first housing to a planar first side of an attachment block; and
rigidly attaching the second housing to a planar second side of the attachment block that is adjacent to the first side of the attachment block to establish a parfocal arrangement among the beam splitter, the fiber port, and the ferrule;
positioning the second housing relative to the first housing to or the parfocal arrangement; and
immobilizing the second housing relative to the first housing by bonding the attachment block to the first housing and the second housing;
wherein the immobilizing comprises:
applying a bonding adhesive on a first attachment surface forming a part of the planar first side of the attachment block;
applying the bonding adhesive on a second attachment surface forming a part of the planar second side of the attachment block; and
positioning the first attachment surface to the first housing and the second attachment surface to the second housing to bond the attachment block to the first housing and the second housing:
detecting a coupling efficiency at the monitoring fiber; and
adjusting a position of the second housing to optimize the coupling efficiency at the monitoring fiber during a curing process of the bonding adhesive.

13. The assembly method of claim 12,
wherein first abutment pads are disposed along a perimeter portion of the first attachment surface and second abutment pads are disposed along a perimeter portion of the second attachment surface, and
wherein the bonding adhesive is titrated on a center portion of the first attachment surface and a center portion of the second attachment surface, such that the bonding adhesive does not interfere with the first and the second abutment pads.

14. The assembly method of claim 12, further comprising:
applying a first biasing force on the attachment block toward the first housing during a curing process of the bonding adhesive; and
applying a second biasing force slightly greater than a weight of the attachment block on the attachment block toward the second housing during the curing process of the bonding adhesive.

15. The assembly method of claim 12, wherein the bonding adhesive has a thermal expansion coefficient equal to or less than that of the first housing, the second housing, and the attachment block.

16. The assembly method of claim 12, wherein each of the first housing, the second housing, and the attachment block comprises precision metal material.

* * * * *